(12) United States Patent
Oscarsson et al.

(10) Patent No.: US 9,389,226 B2
(45) Date of Patent: Jul. 12, 2016

(54) PARTIAL DERIVATIZATION OF PARTICLES

(75) Inventors: Sven Oscarsson, Uppsala (SE); Leif Nyholm, Uppsala (SE); Peter Svedlindh, Uppsala (SE); Klas Gunnarsson, Uppsala (SE)

(73) Assignee: LAB-ON-A-BEAD AB, Lycke (SE)

( * ) Notice: Subject to any disclaimer, the term of this patent is extended or adjusted under 35 U.S.C. 154(b) by 1429 days.

(21) Appl. No.: 12/746,379

(22) PCT Filed: Dec. 15, 2008

(86) PCT No.: PCT/EP2008/067521
§ 371 (c)(1),
(2), (4) Date: Sep. 24, 2010

(87) PCT Pub. No.: WO2009/074692
PCT Pub. Date: Jun. 18, 2009

(65) Prior Publication Data
US 2011/0003401 A1 Jan. 6, 2011

(30) Foreign Application Priority Data

Dec. 13, 2007 (SE) ........................................ 0702790

(51) Int. Cl.
*G01N 33/553* (2006.01)
*G01N 33/543* (2006.01)
*B01J 19/00* (2006.01)

(52) U.S. Cl.
CPC ......... *G01N 33/5434* (2013.01); *B01J 19/0046* (2013.01); *B01J 2219/005* (2013.01); *B01J2219/00466* (2013.01); *B01J 2219/00572* (2013.01); *B01J 2219/00596* (2013.01); *B01J 2219/00648* (2013.01); *B01J 2219/00677* (2013.01); *G01N 2446/20* (2013.01); *Y10T 428/2982* (2015.01)

(58) Field of Classification Search
CPC .................. B01J 19/0046; B01J 2219/00466; B01J 2219/005; B01J 2219/00572; B01J 2219/00596; B01J 2219/00648; B01J 2219/00677; G01N 33/5434; G01N 2446/20; Y10T 428/2982

USPC .................................................... 436/518, 526
See application file for complete search history.

(56) References Cited

U.S. PATENT DOCUMENTS 4,452,773 A * 6/1984 Molday ........................ 424/1.37

FOREIGN PATENT DOCUMENTS

| WO | 03/043931 A1 | 5/2003 |
| WO | 2004/063705 A2 | 7/2004 |
| WO | WO2007064297 | * 7/2007 |

OTHER PUBLICATIONS

Perro et al, Journal of Materials Chemistry, The Royal Society of Chemistry, Cambridge, GB, 15:3745-3760 (Jul. 25, 2005).
Pavlovic et al, Nano Letters, 3(6):779-781 (2003).

* cited by examiner

*Primary Examiner* — Mark Shibuya
*Assistant Examiner* — Pensee Do
(74) *Attorney, Agent, or Firm* — Porter, Wright, Morris & Arthur LLP (57) ABSTRACT

There is disclosed a method for partially derivatizing a curved surface of particles in an electrically conducting solvent, said method comprises the steps: a) bringing particles in close contact with at least one surface by using a force, b) inducing a chemical reaction on at least one part of a particle by applying an electrical potential between said at least one surface and the electrically conducting solvent, and c) further reacting said at least one part of a particle where a chemical reaction has been induced in step b) above. There is further disclosed a partially derivatized particle as well as uses of the particle. Advantages include that the method is simple and only requires a potentiostat in addition to standard laboratory equipment, is inexpensive, time-efficient, and inherently parallel.

18 Claims, 4 Drawing Sheets

PARTIAL DERIVATIZATION OF PARTICLES

RELATED APPLICATION

The present application is a 371 of PCT/EP2008/0067521 filed Dec. 15, 2008.

TECHNICAL FIELD

The present invention relates to an electrochemical method for partial derivatization of the curved surface of particles.

BACKGROUND

Particles with several different functions are sometimes called Janus-particles, named after the Roman god Janus. Janus-particles can be considered a sub-group of the collective term "dis-symmetrical particles", which also includes particles differing in shape and bulk content. Such particles have been studied previously, for instance Zhang et al. patterned 270 and 925 nm polystyrene particles by spreading them in a mono-layer onto a surface, masking them with a mono- or bi-layer of silica particles on top and finally evaporating gold onto the bi- or tri-layer. The bottom layer of polystyrene particles became surface-patterned of gold depending on the packing-pattern of silica-particles on top (G. Zhang et al, Nano Letters 5, No 1 (2005), 143-146). In a continued study by the same group particles with multiple dots (2-5) in symmetric patterns were obtained by increasing the number of particle-layers in combination with reducing the size of the uppermost particles (G. Zhang et al, Angewandte Chemie Int E. 44 (2005), 7767-7770). A microcontact printing technique has been used to synthesize latex particles with dipolar properties. The principle is to spread the particles on a glass slide and have a coating on a PDMS-stamp, which is then pressed against the glass slide. In the first work, negatively charged polystyrene particles were asymmetrically (hemispherical) coated with a cationic surfactant, which bound hydrophobically to the particles, thus making a particle with two opposing charges (O. Cayre et al, Chem Commun, 2003, 2296-2297). In the second work, they used the same method to stamp a layer of 1.5 μm sulphate-coated particles on a hemisphere of 10 μm amine-coated particles (O. Cayre et al, 2003, 2445-2450). Nie et al. synthesized bi- and tri-functional (dis-symmetrical) particles by polymerization of droplets of two or three monomers flowing parallel in streams which passed through a nozzle, making the droplets. The particles produced in this manner were sized 40-100 μm and had a dis-symmetric distribution of the monomers within the particles (Z. Nie et al, 2006, JACS 128, 9408-9412). Matsunaga et al. presented the concept "particles-on-particles", where bacterial magnetic nano-particles (50-100 nm diameter) were bound to the surface of non-magnetic polystyrene particles (6 μm diameter). The surface of the polystyrene particles was coated with streptavidin, which selectively binds to biotin. The surface of the nano-particles was coated partly with biotin, partly with the IgG-binding part of protein A. This system is thus capable of binding IgG from a solution onto nano-particles that are further bound to the surface of particles, which then become magnetic. According to Matsunaga et al, with this strategy it is possible to increase the effective surface area and thus increase the amount of protein bound to a micro-particle by taking advantage of the larger surface/volume ratio of the nano-particles as compared to a micro-particle and at the same time take advantage of the lesser tendency of micro-particles to aggregate and stick onto e.g. pipette surfaces as compared to nano-particles (Matsunaga et al, Analytica Chimica Acta 597 (2007), 337-339). Pregibon et al presented a lithographic method to continuously fabricate and encode dis-symmetrical polymeric particles from a monomer flow in a one-step process. The particles comprised two parts: one encoding part which identified the particle and one probing part to which an analyte could bind. In the simplest case, two parallel laminar flows containing the two monomers were streaming through a channel, in which the monomers were exposed to a UV-burst that induced polymerization at the exposed area. The UV light was passed through an optical mask, which defined the encoding pattern on the particle as well as the particle shape. The stream of monomer which makes up the probing part of the particle also contain the probe, and thus the probing part of the synthesized particles can be directly identified by the written pattern. The particles were mixed with a sample containing fluorescence labeled DNA oligomers, and subsequently passed through a reading device, which identified the pattern on the particle and the presence or absence of fluorescence on the probing part (Pregibon at al., Science 315 (2007) 1393-1396.

Pavlovic et al. used electro contact printing to immobilize proteins in patterns on a thiolated flat silicon surface, by site-selective oxidation of thiols to thiolsulphinates (Nanoletters vol. 3, No. 6, 779-781, 2003).

It is known to modify planar surfaces with thiol groups, where an electrical potential is applied between the planar surface and an electrode close to the surface. As a result thiosulfinate/thiosulfonate groups are formed on the surface. The thiosulfinate/thiosulfonate groups on the planar surface can later be reacted with thiol groups to form covalent bonds.

There is a need of miniaturization of components within nanotechnology, diagnosis, research and development. Within many areas there is a need to store information or attach various molecules on a particle. If it is possible to manufacture particles with a partially derivatized surface, this will open a lot of possible uses.

There are known technologies to store information on larger particles and to derivatize large particles. Regarding partial derivatization of smaller particles, such as particles with a diameter below 100 μm, technical problems arise. One problem is the control of the particle movement. Thus there is a need in the art for a method to manufacture partially derivatized smaller particles.

SUMMARY

It is an object of the present invention to obviate at least some of the disadvantages in the prior art and provide an improved method for partially derivatizing particles.

In a first aspect there is provided a method for partially derivatizing a curved surface of particles in an electrically conducting solvent, said method comprises the steps: a) bringing particles in close contact with at least one surface by using a force, b) inducing a chemical reaction on at least one part of a particle by applying an electrical potential between said at least one surface and the electrically conducting solvent, and c) further reacting said at least one part of a particle where a chemical reaction has been induced in step b) above.

In a second aspect there is provided a partially derivatized particle prepared according to the above method.

In a third aspect there is provided use of a partially derivatized particle prepared according to the above method.

In a fourth aspect there is provided a diagnostic device comprising at least one partially derivatized particle manufactured according to the above method.

In a fifth aspect there is provided a surface comprising a multitude of particles manufactured according to the above method.

Further embodiments are defined in the appended claims, which are specifically incorporated herein by reference.

One advantage of an embodiment is that the method is simple and only requires a potentiostat in addition to standard laboratory equipment.

Another advantage is that the method is inexpensive.

A further advantage is that the method is time-efficient.

Another advantage is that the method is inherently parallel.

BRIEF DESCRIPTION OF THE DRAWINGS

Various embodiments are further illustrated in the attached drawings in which:

FIG. 4 shows fluorescence microscope images of electro oxidized beads: FIG. 4a (10 seconds @ 0.7 V) FIG. 4b: (10 seconds @ 1.0 V).

DEFINITIONS

Before the invention is disclosed and described in detail, it is to be understood that this invention is not limited to particular configurations, process steps and materials disclosed herein as such configurations, process steps and materials may vary. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The following terms are used throughout the description and the claims.

The term "about" as used in connection with a value throughout the description and the claims means that the true value can be up to 10% higher or up to 10% lower than the indicated value.

"Chemical reaction" is used throughout the description and the claims to denote a process that results in the interconversion of chemical substances. The term chemical reaction includes electrochemical reactions.

"Close contact" is used throughout the description and the claims to denote a distance between the particles and the surface which is smaller than 20 nm, preferably smaller than 10 nm and most preferably a distance so small that the particles cannot be moved any further towards the surface.

"Derivatize" is used throughout the description and the claims to denote a process to alter the chemical composition of a compound by a chemical reaction, which changes some part of the molecule. A molecule in a surface layer can be derivatized.

"Electrically conducting solvent" is used throughout the description and the claims to denote any solvent which has the ability to conduct an electric current. Water is an example of an electrically conducting solvent.

"Electrochemical reaction" is used throughout the description and the claims to denote a chemical reaction that is caused by an external electrical potential or a chemical reaction causing an electrical potential.

"Magnetic particle" is used throughout the description and the claims to denote a particle with a magnetic susceptibility. Thus both paramagnetic and ferromagnetic particles are encompassed within the term magnetic particle.

"Particle" is used throughout the description and the claims to denote a small piece of material. The shape of a particle is arbitrary and examples of shapes include spherical, rectangular, cubic, polygonal, and an irregular shape. Particles include bodies with all kinds of geometrical shapes.

"Pattern" is used throughout the description and the claims to denote a form, template, or model on a surface which can be used to make or to generate a corresponding pattern on a particle. Patterns are also related to repeated shapes or objects, sometimes referred to as elements of the series.

DETAILED DESCRIPTION

The present inventors have found an electrochemical method for partial derivatization of the curved surface of particles.

In a first aspect there is provided a method for partially derivatizing a curved surface of particles in an electrically conducting solvent, said method comprises the steps: a) bringing particles in close contact with at least one surface by using a force, b) inducing a chemical reaction on at least one part of a particle by applying an electrical potential between said at least one surface and the electrically conducting solvent, and c) further reacting said at least one part of a particle where a chemical reaction has been induced in step b) above.

In one embodiment the particles are magnetic and a magnetic field is used to bring the particles in close contact with said at least one surface. In one embodiment the particles have magnetic properties so that they can be controlled by an external magnetic field.

The diameter of the particles is in the interval from about 0.02 μm to about 100 μm. In one embodiment the diameter of the particles is from 1 μm to about 100 μm. In an alternative embodiment the diameter of the particles is from 0.02 μm to about 1 μm. In another embodiment the diameter of the particles is from 0.1 μm to about 10 μm. Other intervals for the diameter of the particles include, but are not limited to from about 0.02 μm to about 0.1 μm, from about 0.1 μm to about 1 μm, from about 1 μm to about 10 μm, from about 10 μm to about 100 μm.

In one embodiment the diameter of the particles is below 100 μm. In another embodiment the diameter of the particles is below 10 μm. In another embodiment the diameter of the particles is below 1 μm. 1 μm means $1 \times 10^{-6}$ m.

In one embodiment the size distribution of the particles is monodisperse. In an alternative embodiment the size distribution of the particles is polydisperse.

Examples of materials that the particles are made of include but are not limited to polystyrene and silica. In one embodiment the material is a matrix type material. In one embodiment the material comprises further additives and substances such as magnetic additives. Examples of magnetic materials include but are not limited to a magnetic metal and a magnetic metal-oxide. In one embodiment the particles are made of a matrix type material further comprising smaller particles in the nano-size range, i.e. in the order of $10^{-9}$ m. In one embodiment the particles in the nano-size range are made of magnetic metal and/or magnetic metal-oxide.

In one embodiment the particles are coated. In one embodiment the particles are coated with a polymer. In another embodiment a core comprising nanoparticles in a matrix material are coated with a polymer. In one embodiment the core comprises nanoparticles of iron oxide ($Fe_2O_3$ and/or $Fe_3O_4$). Examples of polymers which can be used to coat the particles include but are not limited to agarose, dextran, latex, polyethylene glycol and hyaluronic acid.

In one embodiment the particles are non-conducting. In an alternative embodiment the particles are conducting. In a further embodiment the particles are made of a mixture of conducting and non-conducting material. In one embodiment the particles are made of a conducting core with a non conducting coating, the thickness of which can be varied.

The particles are in close contact with at least one surface. In one embodiment the particles are near the at least one surface at a distance up to 20, preferably up to 10 nm. A distance between the particle and the surface up to 20 nm, preferably 10 nm is to be encountered in the term "close contact." In one embodiment the particles are so close to the surface that they cannot be moved towards the at least one surface.

In one embodiment the particles are in close contact when the process starts. In an alternative embodiment the particles are first moved towards the at least one surface using a force. In one embodiment the force is a result of a magnetic field exerting a force on magnetic particles.

In one embodiment the particles are kept in close contact with the at least one surface using magnetic attraction. When using magnetic attraction, for instance a permanent magnet or an electromagnet is used to create a magnetic field which is used to control the particles. In one embodiment an electromagnet is used, making it easy to control the magnetic field. In another embodiment a permanent magnet is used.

The surface of the particles comprises groups which can be oxidized to generate functional groups. Examples of such groups include but are not limited to SH groups, $NH_2$ groups, COOH groups, aromatic groups, and OH groups. In one embodiment the surface of said particles comprises SH groups, i.e. thiol groups. In one embodiment the surface of the particles comprises hydroxyl groups, which are oxidized to aldehydes. The aldehydes are reactive towards amino groups in proteins or peptides with formation of a Schiff base.

In an alternative embodiment the surface of the particles comprises groups which can be reduced to generate functional groups. Examples of such groups include but are not limited to disulfide groups and $NO_2$ groups. In case of groups which can be reduced a negative electric potential is used to reduce the groups.

In one embodiment the at least one surface comprises at least one material selected from the group consisting of copper, silver, gold, platinum, iridium, osmium, palladium, rhodium, a carbon based material, and a metal oxide. In one embodiment the at least one surface is a gold surface. In an alternative embodiment the at least one surface is a platinum surface.

The chemical reaction induced on a patch of a non-conducting particle by applying an electrical potential is dependent on the distance between the at least one surface and the patch. A chemical reaction will be induced to a greater extent on parts of the particle which are close to the surface. For parts on the particle which are further away from the surface a chemical reaction is induced to a lesser extent. For a conducting particle the effect of the distance is lesser. In one embodiment the chemical reaction is controlled by selecting the material in the particles to obtain the desired conductivity. Thus there is provided derivatization of particles wherein the conductivity of the particles is adjusted.

In one embodiment the chemical reaction which is induced by applying an electrical potential is an electrochemical reaction.

In one embodiment the electric potential is kept constant during the reaction. In an alternative embodiment the electric current is kept constant by varying the electric potential. In a further embodiment the potential is varied during the reaction. In an alternative embodiment the electric current is varied during the reaction.

The time during which an electric potential is applied can vary within wide boundaries. The time can be adjusted within wide boundaries. One non limiting example of a reaction time is from about 0.01 to about 10 seconds. Examples of reaction times include, but are not limited to 0.1, 1, 3, 6, and 10 seconds.

Particles with a patch where a chemical reaction has been induced are thus created. The patches where a chemical reaction has been induced are then able to participate in another chemical reaction. The size of a patch where a chemical reaction has been induced is in one embodiment typically from about 1 to about 1000 $nm^2$. For larger particles even larger areas are obtainable.

The rest of the surface where electro oxidation has not taken place can be used for immobilization of at least one other kind of molecules provided with SS-pyridyl groups since the rest of the surface which is still intact after electro oxidation contains thiols and these are reactive towards SS-pyridyl groups. These circumstances can be useful for immobilization of two or more different kinds of molecules.

In one embodiment the area of a patch is controlled by varying the magnetic field and/or the reaction time.

In one embodiment the area of a patch is controlled by varying the reaction time of the magnetic field.

The size of the patches where a chemical reaction has been induced is adjusted by using at least one of the following methods: adjustment of the conductivity of the particles, adjustment of the magnetic field for magnetic particles, and the particles size.

In one embodiment the electrical potential used to induce the chemical reaction is from about −1 to about +5 V. In another embodiment the electrical potential is from about −0.4 to about +2 V. In yet another embodiment the electric potential is from about −0.1 to about +1.2 V. In a further embodiment the electric potential is from about +0.2 to about +0.8 V. The electric potentials in aqueous media are measured against an Ag/AgCl reference electrode. For non-aqueous media even higher electric potentials can be used. A person skilled in the art realizes that also other voltages can be used to oxidize chemical groups on the surface of the particles. The above intervals are merely examples of suitable intervals. For oxidation of chemical groups on the surface of the particles a sufficiently positive potential is preferably used, whereas for reduction of groups on the surface a sufficiently negative potential is preferably used.

If the surface of the particles comprises thiol groups then thiosulfinate/thiosulfonate groups will be formed on the surface of the particles on the parts of the particles which are close to the surface during the oxidation. The thiosulfinate/thiosulfonate groups are able to react with thiol groups to form covalent bonds.

In one embodiment molecules are bound to the patch of the particle where a chemical reaction has been induced.

In one embodiment molecules comprising at least one thiol group are bound to the patch of the particle where thiosulfinate/thiosulfonate groups have been formed. Thus the further reaction of those parts of the surface of the particles where an electrochemical reaction has been induced, comprises a reaction between a thiol group on a molecule and thiosulfinate/thiosulfonate group on said particles.

In one embodiment at least one molecule is covalently bound to the parts of said surface where a chemical reaction has been induced. The molecule to be bound to the particle is in one embodiment selected from aliphatic and aromatic molecules comprising heteroatoms such as nitrogen, hydrogen, carbon, sulphur, oxygen as well as metals or metal ions, macrocyclic molecules, proteins, fragments and agglomerate of molecules such as inclusion bodies. In an alternative embodiment the molecule to be bound to the particle is at least one molecule selected from an aliphatic molecule optionally comprising at least one heteroatom, an aromatic molecule optionally comprising at least one heteroatom, and a macrocyclic molecule. The entity to be bound to the particle is in another embodiment selected from bacteria and virus such as lactic acid bacteria optionally in combination with other bacteria, cells, mast cells, macrophages, and nerve cells. In one embodiment the molecule is at least one entity selected from the group consisting of an amino acid, an antibody, a bacterium, a cell, a detectable molecule, DNA, RNA, a fluorescence marker, a peptide, a porfyrine, a phtalocyanine, a protein and vitamin B12.

The method for manufacturing a partially derivatized particle is in one embodiment repeated for the same particle so that several different derivatized patches are created. Thus the process is repeated to obtain particles with at least two parts where a chemical reaction has been induced. Many different patches can be created on one particle. In one embodiment one particle comprises patches with at least two different covalently bound molecules. This is in one embodiment achieved by using magnetic particles in connection with a magnetic field, where the magnetic field is varied or switched on and off. Alternatively a flow cell is used, where the particles hit the surface electrode several times when passing through the flow cell.

In one embodiment the particles are contacted with the at least one surface several times in order to create several patches. In one embodiment a sufficiently high electric potential is used which causes the particles to be contacted with the at least one surface several times as a result of the convection induced by oxygen or hydrogen evolution. Examples of such potential include but are not limited to +1.5, +2, +2.5, −1.5, and −2 volts.

In one embodiment the at least one surface comprises at least one pattern. This pattern is able to give a corresponding pattern of those parts of said surface where a chemical reaction has been induced. Examples of patterns include but are not limited to a bar code. Particles can thus be marked with an individual pattern, which makes it possible to distinguish different particles. There is a possibility to identify individual particles. An area comprising a pattern can be provided with molecules, which molecules are possible to detect.

In one embodiment the at least one surface comprises at least one microstructured electrode. The microstructured electrode is able to induce a pattern on the particles.

In one embodiment the at least one surface, which the particles are kept in close contact with, determines the pattern on the particles. The pattern on the at least one surface gives rise to a pattern on the particles.

In one embodiment the at least one surface comprises a first and a second material in a bilayer, wherein the first material is selected from the group consisting of copper, silver, gold, platinum, iridium, osmium, palladium, rhodium, a carbon based material and a metal oxide, and wherein the second material is selected from the group consisting of iron, nickel, cobalt, a magnetic transition metal alloy and a magnetic oxide.

In one embodiment particles are rotated during the derivatization and/or between derivatizations. This will increase the possibilities to create various patterns on the particles. Means of inducing rotation include but are not limited to a magnetic field.

In one embodiment with magnetic particles, the magnetization of the particles is remanent.

In another aspect there is provided partially derivatized particles prepared according to the described method.

In one embodiment at least two different drugs are attached to the particle. Examples of drugs include but are not limited to drugs against cancer and antibiotics. By the combination of at least two drugs a local synergistic effect is achieved.

In a third aspect there is provided use of a partially derivatized particle in a diagnostic device. In one embodiment the partially derivatized particle is used in a diagnostic device outside the human or animal body.

There is also provided use of partially derivatized particles as markers to identify specific particles.

There is provided use of partially derivatized particles, wherein the particles are rotated while signals from the particles are measured. Means of inducing rotation include but are not limited to a magnetic field. An example of this includes particles partially derivatized with fluorescent molecules that are rotated during detection of light form the fluorescent molecules.

In a fourth aspect there is provided a diagnostic device comprising partially derivatized particles manufactured according to the present method.

In one embodiment molecules with different physical and/or chemical properties are attached to different parts of the surface. In one embodiment a particle comprises hydrophobic molecules on one side and hydrophilic molecules on another side. In one embodiment a lot of such particles are placed as a monolayer on a surface and makes it possible to vary the properties of the surface by rotating the particles. In one embodiment particles on a surface are rotated to change the properties of the surface from hydrophilic to hydrophobic.

In one embodiment a multitude of the partially derivatized particles according to the present method are at a surface and are rotated to vary the properties of the surface.

In one embodiment there is provided a surface comprising a multitude of particles manufactured according to the present method.

In one embodiment particles at a surface are rotated locally using local fields, thereby changing the properties of the surface.

There are a lot of different application areas for the present method and the particles manufactured therewith. Examples include but are not limited to:

Tracking and/or identification; methods by which transportation mechanisms can be investigated, e.g. transportation in the human body and organs, tracking during manufacturing processes, tracking of pollutions, tracking methods for food processing and tracking methods for protection of brands, original pharmaceutics, drugs and waste of oil. One advantage of magnetic particles is the possibility to concentrate particles in diluted solutions by passing large volumes through a magnetic trap.

Cancer treatment; Different drugs are attached to one and the same particle in order to achieve an enhanced local synergistic effect of the combination.

Antibiotic treatment; by attaching several different types of antibiotics to one and the same particle, an enhanced local synergistic effect of the combination is achieved.

Diagnostics; Flow cytometry and FACS. Marking several different types of cells with particles with different codes where each code corresponds to one type of cells. A large number of cells can be identified by FACS and flow cytometry which have a very large capacity to identify and sort cells (such as 50 000 cells per minute).

ELISA; Instead of one type of particle in each well, many (such as, but not limited to several hundred) different types of particles are added in each well and thus many different antigens are diagnosed in each well.

Control of chemical/biochemical processes; If magnetic particles with remanent magnetizing are used, partial derivatization of the particle can still be performed and further the remanent magnetization of the particles makes it possible for the particle to orient in a magnetic field in a reproducible manner. This can be used so that a particle is allowed to orient the derivatized part of the particle surface towards a corresponding surface where a counterpart for a chemical reaction is present. For instance for catalysis where the catalyst is on the surface of the particles and the substrate in a fluid which the particle partially is in contact with.

Other features and uses of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Experimental

Monodisperse magnetic particles commercially available from Micromod® GmbH under the trade name Micromer® were washed. The particles consist of iron oxide nanoparticles in an organic matrix coated with a polymer layer for encapsulation.

IgG labeled with fluorescin was thiolated to introduce SH groups.

Figure 2:
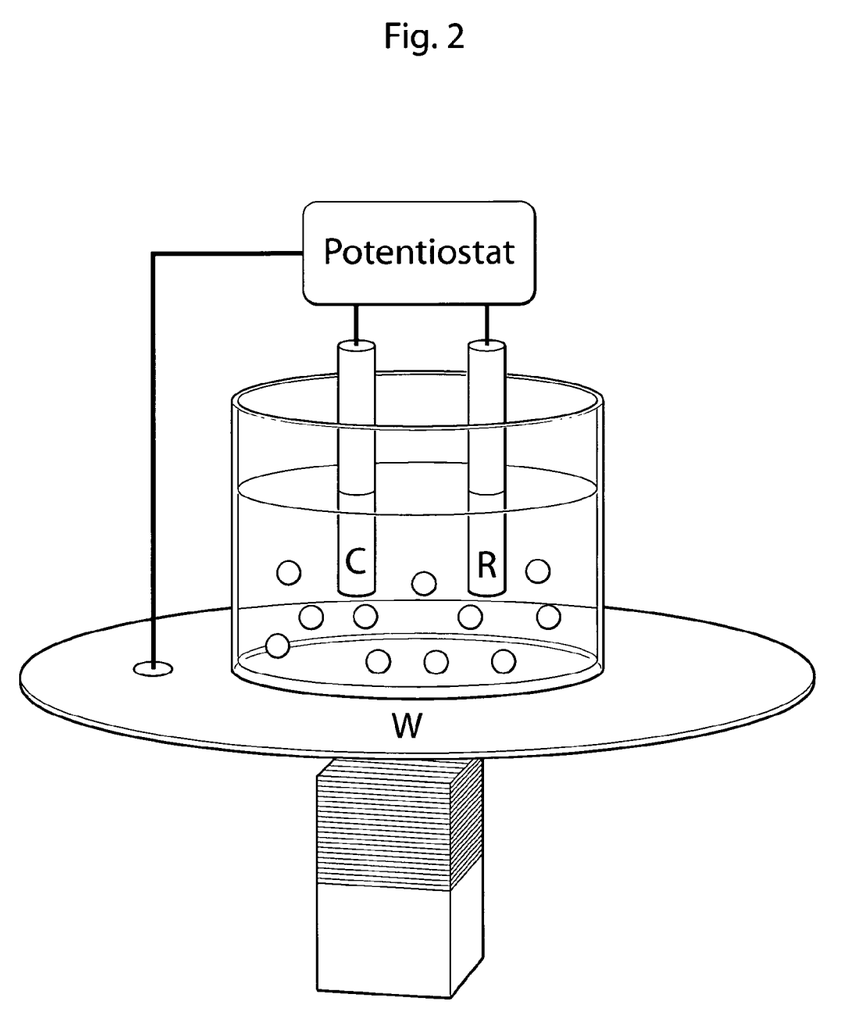
FIG. 2 shows an experimental setup for electro oxidation as used in the examples.

The setup for electro oxidation consisted of a polytetrafluoroethene cylinder of 13 mm diameter mounted on top of a gold-plate. A homogenous (less than 10% gradient in the plane) magnetic field of 60 mT was applied orthogonally to the gold-plate by using a permanent magnet mounted under the gold-plate. The gold wire counter electrode and the Ag/AgCl reference electrode were placed in the reaction cell. The gold plate was used as the working electrode in a potentiostatic set-up by connecting the potentiostat to the gold-plate outside of the reaction cell. The oxidations were carried out in a phosphate buffer with pH 7.0. See FIG. 2 for a schematic representation of the experimental setup. Suspended magnetic beads are in this embodiment distributed on the working electrode (W) as a result of the presence of an external magnet underneath. The potential of the working electrode is applied versus the reference electrode (R) employing the potentiostat which also measures the current between the working electrode and the counter electrode (C).

Figure 1:
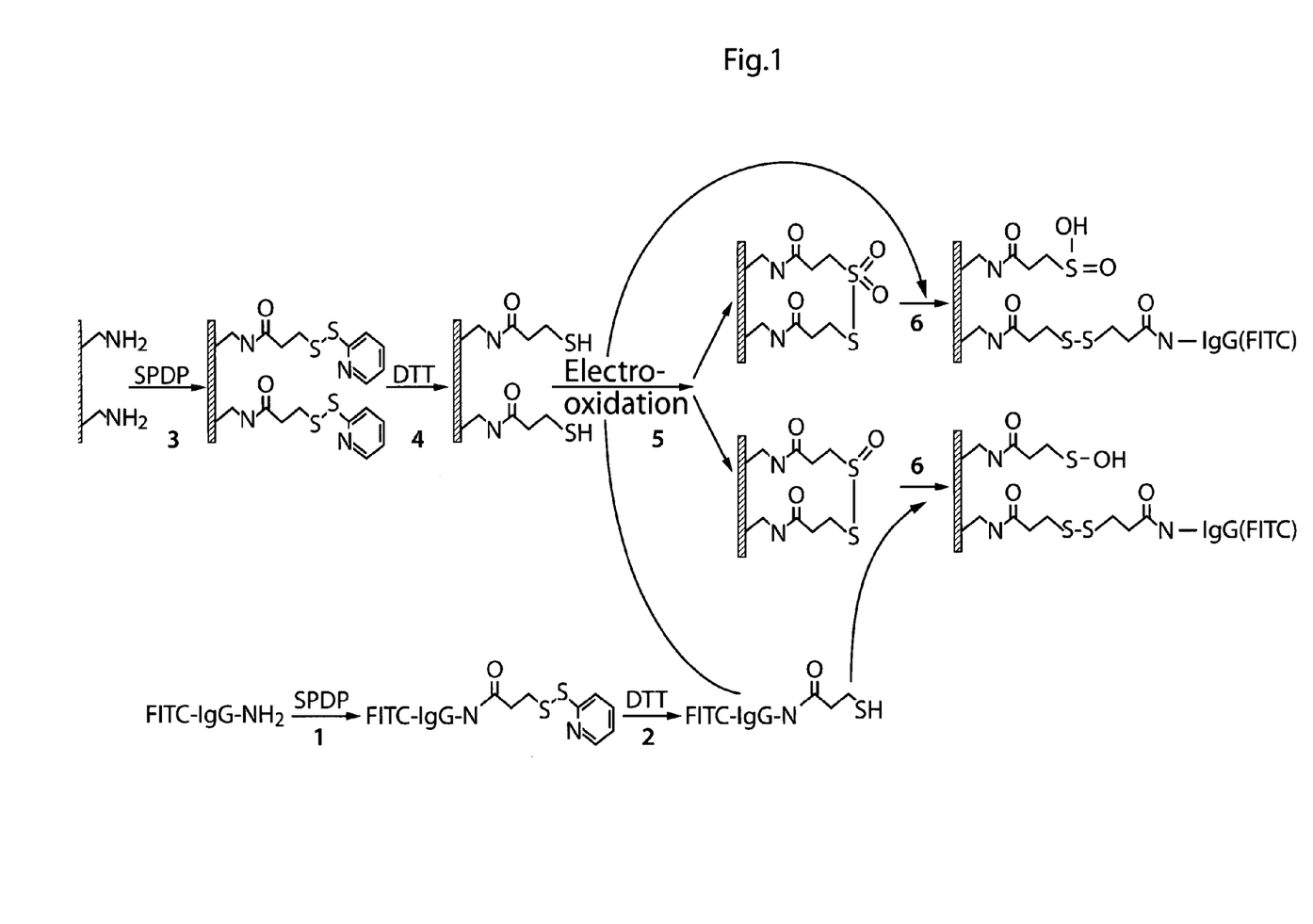
FIG. 1 shows a reaction scheme for one embodiment.

Electro oxidation of thiols on magnetic particles 2 ml of the thiolated particles was added to the reaction cell and allowed to distribute on the gold surface by gravity/magnetic field for 2 min. A potential of +0.7 V versus the Ag/AgCl reference electrode was applied for 10 s. The particles were thereafter resuspended and the volume reduced to 50 μL by collecting the particles with a permanent magnet. The particle suspension was immediately mixed with 50 μL freshly prepared thiolated IgG labeled with fluorescin and incubated over night. The electro oxidation procedure was repeated on three samples. See FIG. 1 for a reaction scheme for partial immobilization of FITC labeled IgG to electro activated thiolsulphinates/thiolsulphonates on magnetic particles. Thiol activation of IgG and magnetic particles is in this embodiment produced via N-Succinimidyl 3-(2-pyridyldithio)-propionate (SPDP) conjugation to amino groups followed by dithiothreitol (DTT) treatment. The thiol reactive thiolsulphinates/thiolsulphonates on the surface on magnetic particles are generated by electro oxidation.

As reference, 10 μL of particles with thiol groups on the surface was mixed with 50 μL thiolated IgG labeled with fluorescin and incubated over night.

Figure 4A:
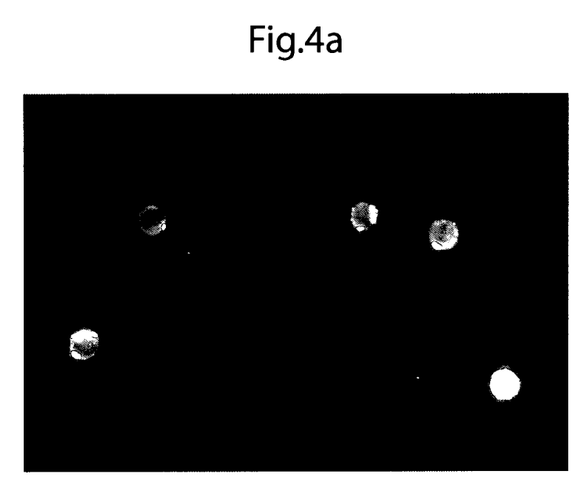

Partially electro oxidized particles treated with thiolated IgG labeled with fluorescin resulted in spots with strong fluorescence on the particle surface, see FIG. 4a.

Figure 3:
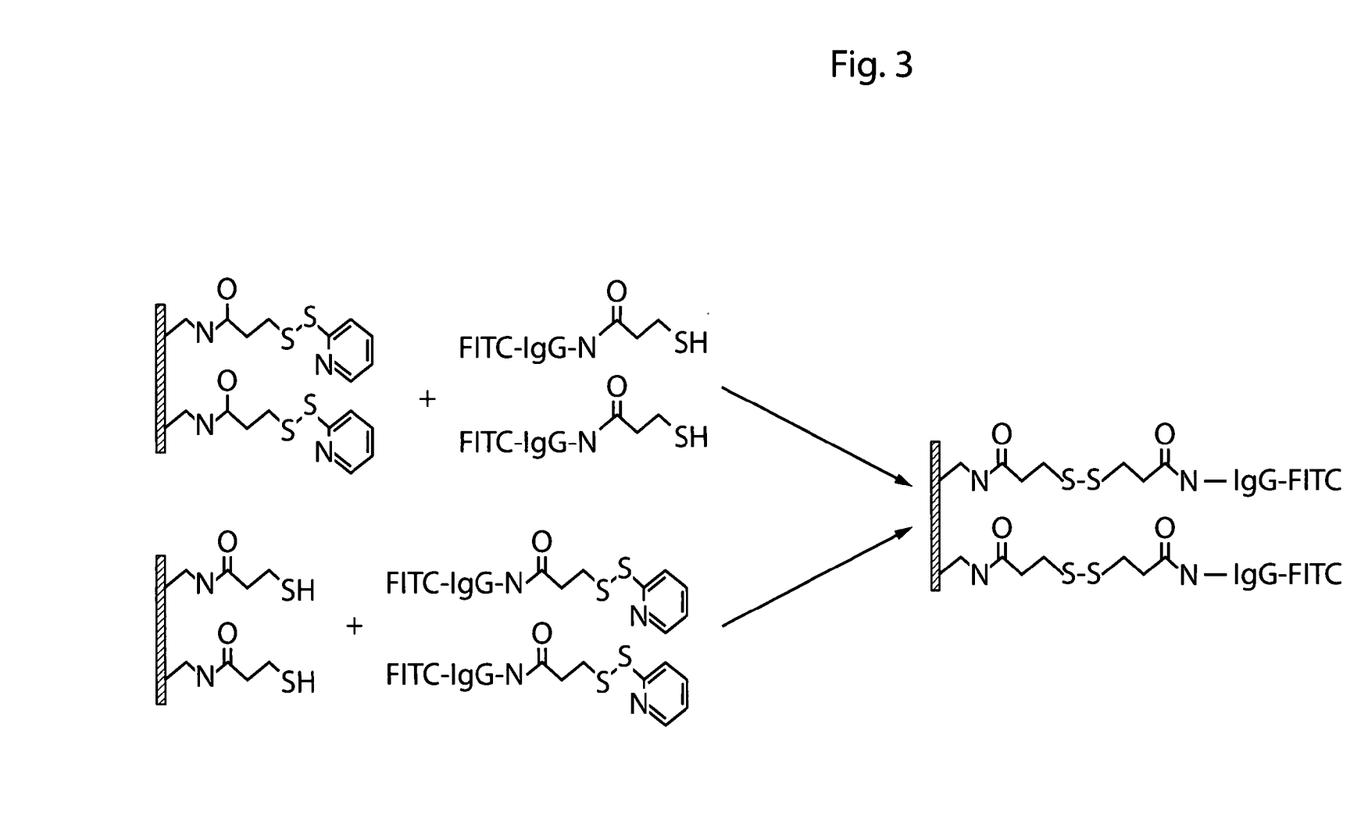
FIG. 3 shows a reaction scheme for positive control experiments for verification of the presence of thiols on beads and proteins.

The reference reaction between the particles with SS-pyridyl groups on the surface and thiolated IgG labeled with fluorescin resulted in a strong, evenly distributed fluorescence over the entire particle surface. See the reaction scheme for the reference reaction in FIG. 3. Particles containing SS-pyridyl groups will not be oxidized to thiosulfinate or thiosulfonate. They will be intact and they react with IgG containing thiol groups. The result was a strong evenly distributed fluorescence over the entire particle surface.

In another reference reaction particles were provided with thiol groups and IgG was modified with SS-pyridyl groups and fluorescin. IgG with SS-pyridyl groups will react with thiols but not with thiosulfinate/thiosulfonate. The result was a strong evenly distributed fluorescence over the entire particle surface.

Example 2

Example 1 was repeated but a potential of +0.8 V was used for 10 s which resulted in a higher amount of patterned particles and a higher amount of particles with two or several spots. The intensity of the homogeneous fluorescence was also increased when increasing the potential from +0.7 to +0.8 V.

Example 3

Example 2 was repeated but without any magnetic field. This resulted in a higher amount of particles with several spots which can be explained by movement of the particles during the oxidation step. This shows that the presence of the magnetic field facilitates the attainment of particles with only one spot.

Example 4

Example 1 was repeated but a potential of +0.8 V was used for 3 and 6 seconds respectively. This resulted in particles with spots similar to those obtained with an oxidation potential of +0.7 V and oxidation duration of 10 s.

Example 5

Example 1 was repeated but a potential of +0.7 V was used for 1 s. This resulted in particles with spots similar to those obtained with an oxidation time of 10 s.

Example 6

Example 1 was repeated but a potential of +0.7 V was used for 0.1 s. This resulted in particles with spots similar to those obtained with an oxidation time of 10 s indicating that the oxidation of the particles is fast as can be expected for a surface confined oxidation reaction.

Example 7

Figure 4B:
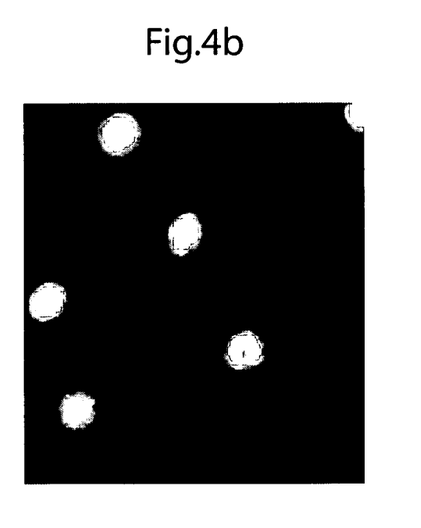

Example 1 was repeated but a potential of +1.0 V was used for 10 s. This resulted in a higher amount of patterned particles and a higher amount of particles with two or several spots. The intensity of the homogeneous fluorescence was also increased. See FIG. 4b.

Example 8

Example 1 was repeated but the potential was varied from −0.2 V to +1.2 V and back again at a rate of 50 mV/s. This gave rise to a mixture of particles with different number of spots and with high homogeneous fluorescence intensity.

Example 9

Example 1 was repeated with a stronger magnetic field. This resulted in particles exhibiting only one spot indicating that the magnetic field indeed can be used to ensure that the particles do not move during the oxidation step. This facilitates the manufacturing of particles with a predefined number of spots.

Example 10

Example 1 was repeated using five consecutive oxidation steps between which the particles were detached from the gold surface by removing the magnet and stirring the solution. This gave rise to particles with five spots.

Example 11

Example 1 was repeated with an electrolyte with a pH value of 5.0. This gave rise to particles with spots similar to those obtained at pH 7.0 but with higher homogeneous fluorescence intensity.

The invention claimed is:

1. A partially derivatized particle prepared by a method for partially derivatizing a curved surface of particles in an electrically conducting solvent, said method comprising the steps:
   a. bringing particles in close contact with at least one surface by using a force,
   b. inducing a chemical reaction on at least one part of a particle by applying an electrical potential between said at least one surface and the electrically conducting solvent, and
   c. further reacting said at least one part of a particle where a chemical reaction has been induced in step b) to covalently bind molecules thereto,
   wherein the sequential steps a, b, and c are repeated, with repeated steps b and c directed to another at least one part of the particle to covalently bind different molecules thereto, wherein the particle has at least two different derivatized patches, wherein the covalently bound molecules on one of the two patches differ from the covalently bound molecules on the other of the two patches, wherein the covalently bound molecules on each patch are covalently bound to the same type of chemical groups on the particle, and wherein the at least two patches form a pattern.

2. The partially derivatized particle according to claim 1, wherein said particles are magnetic and a magnetic field is used to bring the particles in close contact with said at least one surface.

3. The partially derivatized particle according to claim 2, wherein the magnetization of the particles is remanent.

4. The partially derivatized particle according to claim 1, wherein the diameter of the particles is below 100 μm.

5. The partially derivatized particle according to claim 1, wherein the surface of said particles comprises at least one chemical group selected from the group consisting of a —SH, —NH$_2$, —COOH, —OH, and an aromatic group.

6. The partially derivatized particle according to claim 1, wherein the surface of said particles comprises —SH groups.

7. The partially derivatized particle according to claim 1, wherein said at least one surface comprises at least one material selected from the group consisting of copper, silver, gold, platinum, iridium, osmium, palladium, rhodium, a carbon based material, and a metal oxide.

8. The partially derivatized particle according to claim 1, wherein the further reaction in step c) comprises a reaction between a thiol group on a molecule and a thiosulfinate/thiosulfonate group on said particles.

9. The partially derivatized particle according to claim 1, wherein at least one of said molecules is selected from the group consisting of an aliphatic molecule, an aromatic molecule, and a macrocyclic molecule.

10. The partially derivatized particle according to claim 1, wherein at least one of said molecules is selected from the group consisting of an amino acid, an antibody, a bacteria, a cell, a detectable molecule, DNA, RNA, a fluorescence marker, a peptide, a porfyrine, a phthalocyanine, a protein and vitamin B12.

11. The partially derivatized particle according to claim 1, wherein said at least one surface comprises at least one pattern.

12. The partially derivatized particle according to claim 11, wherein said at least one surface pattern determines the pattern on the particles.

13. The partially derivatized particle according to claim 1, wherein said at least one surface comprises at least one microstructured electrode.

14. The partially derivatized particle according to claim 1, wherein the at least one surface comprises a first material and a second material in a bilayer, wherein the first material is selected from the group consisting of copper, silver, gold, platinum, iridium, osmium, palladium, rhodium, a carbon based material and a metal oxide, and wherein the second material is selected from the group consisting of iron, nickel, cobalt, a magnetic transition metal alloy and a magnetic oxide.

15. The partially derivatized particle according to claim 1, wherein at least two different drugs are attached to the particle.

16. The partially derivatized particle according to claim 1, wherein the particle is marked to facilitate identification.

17. The partially derivatized particle according to claim 1, wherein the particle is rotatable during reading of signals from the particle.

18. A partially derivatized particle comprising at least two different derivatized patches having covalently bound molecules at the patches, wherein the covalently bound molecules on one of the two patches differ from the covalently bound molecules on the other of the two patches, wherein the covalently bound molecules on each patch are covalently bound to the same type of chemical groups on the particle, wherein the diameter of the particles is from about 0.02 to about 100 µm, and wherein the at least two patches form a pattern.

\* \* \* \* \*